US012751848B2

(12) United States Patent
Panzer et al.

(10) Patent No.: US 12,751,848 B2
(45) Date of Patent: Oct. 6, 2026

(54) MULTI-PART SUPPORT DEVICE FOR AN ORTHOSIS

(71) Applicant: BAUERFEIND AG, Zeulenroda-Triebes (DE)

(72) Inventors: Dominique Panzer, Zeulenroda-Triebes (DE); Oliver Marx, Zeulenroda-Triebes (DE); Hans B. Bauerfeind, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 332 days.

(21) Appl. No.: 18/705,425

(22) PCT Filed: Oct. 21, 2022

(86) PCT No.: PCT/EP2022/079402
§ 371 (c)(1),
(2) Date: Apr. 26, 2024

(87) PCT Pub. No.: WO2023/072759
PCT Pub. Date: May 4, 2023

(65) Prior Publication Data
US 2025/0127644 A1 Apr. 24, 2025

(30) Foreign Application Priority Data
Oct. 29, 2021 (DE) ........................ 102021212273.6

(51) Int. Cl.
*A61F 5/01* (2006.01)

(52) U.S. Cl.
CPC .......... *A61F 5/0109* (2013.01); *A61F 5/0125* (2013.01); *A61F 2005/0167* (2013.01)

(58) Field of Classification Search
CPC ........ A61F 5/0109; A61F 5/01; A61F 5/0125; A61F 5/028; A61F 5/05866; A61F 2/50;
(Continued)

(56) References Cited

U.S. PATENT DOCUMENTS 4,202,327 A * 5/1980 Glancy .................. A61F 5/022
602/19
4,508,110 A * 4/1985 Modglin ................ A61F 5/022
2/908
(Continued)

FOREIGN PATENT DOCUMENTS

CN 209253271 U 8/2019
DE 102014113363 A1 * 3/2016 ........... A61F 5/0113
(Continued)

OTHER PUBLICATIONS

European Patent Office acting as International Searching Authority, "International Search Report and Written Opinion," for International Application No. PCT/EP2022/079402, Jan. 25, 2023 and English translation.
(Continued)

*Primary Examiner* — Seema Mathew
(74) *Attorney, Agent, or Firm* — Dentons Durham Jones Pinegar; Sarah W. Matthews

(57) ABSTRACT

The present invention relates to orthopaedic products, in particular orthoses and support devices for orthoses. The invention provides an improved support device for an orthosis, a method of producing the same and an orthosis containing a support device according to the invention.

10 Claims, 5 Drawing Sheets

(58) Field of Classification Search
CPC ........ A61F 5/03; A61F 5/0585; A61F 5/3723; A61F 5/3738
See application file for complete search history.

(56) References Cited

U.S. PATENT DOCUMENTS

| | | | | |
|---|---|---|---|---|
| 5,445,602 | A * | 8/1995 | Grim | A61F 5/012 602/6 |
| 6,319,216 | B1 * | 11/2001 | Coligado | A61F 5/028 602/5 |
| 6,840,916 | B2 * | 1/2005 | Kozersky | A61F 5/022 602/5 |
| 6,932,780 | B2 * | 8/2005 | Kozersky | A61F 5/022 602/5 |
| 7,364,558 | B2 * | 4/2008 | Weaver, II | A61F 5/028 602/19 |
| 11,253,382 | B2 * | 2/2022 | Omarsson | A61F 5/0106 |
| 2003/0220594 | A1 * | 11/2003 | Halvorson | A61F 5/03 602/19 |
| 2004/0068215 | A1 * | 4/2004 | Adelson | A61F 5/0123 602/26 |
| 2004/0077981 | A1 * | 4/2004 | Weaver, II | A61F 5/028 602/19 |
| 2004/0220503 | A1 * | 11/2004 | Kozersky | A61F 5/022 602/19 |
| 2005/0165338 | A1 | 7/2005 | Iglesias et al. | |
| 2006/0079821 | A1 | 4/2006 | Rauch | |
| 2008/0262401 | A1 | 10/2008 | Wagner et al. | |
| 2011/0288611 | A1 * | 11/2011 | Lunau | A61N 1/0408 602/5 |
| 2013/0303955 | A1 * | 11/2013 | Beitl | A61F 5/024 602/19 |
| 2016/0317083 | A1 | 11/2016 | Deluke et al. | |
| 2018/0116856 | A1 * | 5/2018 | Ingimundarson | A61F 5/028 |

FOREIGN PATENT DOCUMENTS

| | | | | |
|---|---|---|---|---|
| DE | 102014113366 | A1 | 3/2016 | |
| EP | 2878284 | A1 | 6/2015 | |
| EP | 2866748 | B1 | 12/2016 | |
| EP | 3285647 | B1 | 9/2019 | |
| EP | 3695857 | A1 | 8/2020 | |
| WO | WO-2014001493 | A1 * | 1/2014 | A61F 5/022 |
| WO | 20210171252 | A1 | 9/2021 | |
| WO | WO-2021171252 | A1 * | 9/2021 | A61F 5/022 |
| WO | WO-2021245026 | A1 * | 12/2021 | A61F 5/0111 |

OTHER PUBLICATIONS

German Patent Office, "Search Report," for German Application No. 10 2021 212 273.6.

European Patent Office acting as International Searching Authority, "International Preliminary Report on Patentability," for International Application No. PCT/EP2022/079402, Oct. 31, 2023.

* cited by examiner

MULTI-PART SUPPORT DEVICE FOR AN ORTHOSIS

CROSS REFERENCE TO RELATED APPLICATIONS

This application is a U.S. a national stage application under 35 U.S.C. 371 of PCT/EP2022/079402 ("the '402 PCT application"), filed Oct. 21, 2022, which claims priority to German patent application DE 10 2021 212 273.6 filed Oct. 29, 2021 ("the '273.6 Priority Application"). The contents of the '402 PCT Application and '273.6 Priority Application are incorporated herein in their entireties.

FIELD OF THE DISCLOSURE

The present disclosure relates to orthopaedic products, in particular orthoses and support devices for orthoses. The disclosure provides an improved support device for an orthosis, a method of producing the same and an orthosis containing a support device according to the disclosure.

BACKGROUND

Orthoses are therapeutic means for stabilising or supporting the movement function of body parts. When providing functional orthoses, the focus is on restoring and/or obtaining mobility of the musculoskeletal system. Orthoses can have a functionally safe, mobilising, supporting, movement-limiting and/or corrective effect on the musculoskeletal system. Orthoses can be used directly post-traumatically, post-operatively or conservatively, i.e. to rebuild, secure or protect joint function, for example in the case of degenerative diseases. In order to achieve the stability required depending on the application, one or more stabilisation elements are provided in the orthosis, which are generally configured essentially in the form of rods or shells. The stabilisation elements configured as shells encompass the body part or body joint to be stabilised, for example an extremity joint, or the torso in the area of the lumbar spine, usually around more than half of its circumference.

The stabilisation elements support the mechanical stabilising effect of the orthosis. Orthoses with stabilisation elements encompassing body parts are for example functional orthoses for ankles, knee joints, hips and thighs, wrists, elbows and shoulder joints. Such orthoses are characterised in particular by the fact that they generally fully encompass the body part to be stabilised, i.e. in particular at least more than half of the circumference of the body part. The stabilisation elements encompassing the body configured for such orthoses are usually shaped brace-shaped and have a circumferential cross-section comprising more than a semicircle (greater than 180 degrees) around the body part to be encompassed.

The stabilisation elements are usually formed from a thermoplastic or thermosetting plastic or composite material. Such non-planar or shell-shaped or curved braces that are configured to functionally encompass the body or body part have an undercut. Such spatial structures are difficult to produce in terms of manufacturing technology. In known production processes, braces encompassing the body or body parts are usually formed from flat blanks (plates) by thermoforming, in particular by deep drawing, into the final spatial end shape (usage conformation) that encompasses the body or body parts. The manufacturing is complex and generally involves a high level of material and personnel input. Stabilisation braces for orthoses configured in the known manner are not accessible to alternative and, in particular, economical manufacturing techniques. There is therefore a need to provide improved stabilisation elements for orthoses which can be produced using simpler and more economical manufacturing techniques and which have at least equivalent and preferably improved functional properties compared to known stabilisation elements.

Plastic injection moulding technology for producing stabilisation elements for orthoses is known in the prior art. However, injection-moulded elements are usually essentially flat configured small and add-on parts or shells that are in no relation to a stabilisation element encompassing the body.

The technical problem underlying the disclosure therefore consists in particular in developing a support device for an orthosis encompassing the body or body parts in such a way that it is simpler and more economical to produce and, depending on the specific embodiment, can simplify the application and/or extend the functional scope of the orthosis.

SUMMARY

The technical problem is solved by the subject matter of the independent claims.

In particular, the present disclosure relates to a support device for an orthosis which is configured to predominantly encompass a body part in its total circumference and comprises two stabilisation elements which each extend over less than half of the total circumference of the body to be encompassed, wherein the support device is characterised in that in that the two stabilisation elements of the support device are positively connected to one another via at least one snap-in connection, wherein at least one of the two stabilisation elements has at least one snap-in hook and the other of the two stabilisation elements has at least one retaining element and wherein the at least one snap-in connection is configured by engagement of the at least one snap-in hook in the at least one retaining element.

DETAILED DESCRIPTION

Figure 1A:
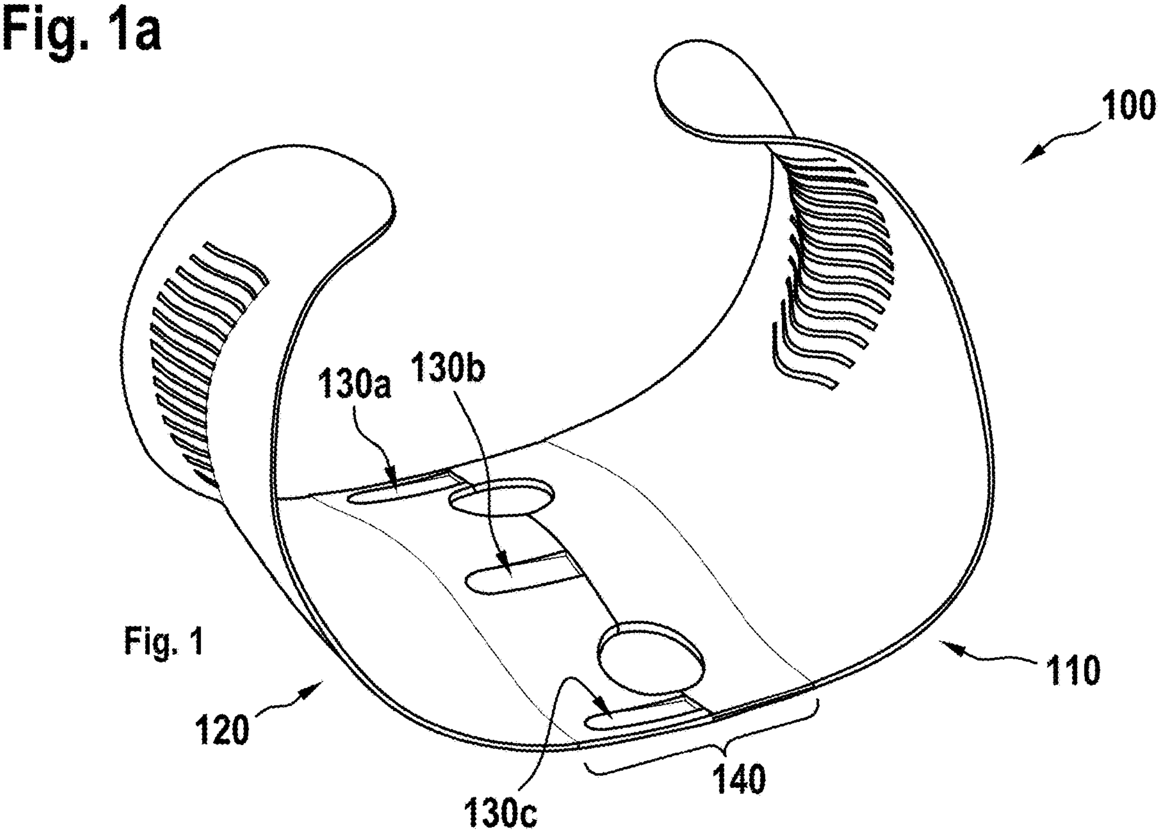
FIG. 1*a* schematically shows the inside of a support device according to the disclosure for a lumbar back orthosis for the human body.

By this particular embodiment of the support device encompassing the body according to the present disclosure, it is advantageously possible to achieve the desired shape and function of the support device by a positively connecting of two stabilisation elements, so that a simple and economical production of the individual stabilisation elements by means of injection moulding is possible and at the same time the functionality and stability of one-piece support devices for n orthoses is maintained or improved. It is particularly advantageous here that the assembly, i.e. the positively connecting, of the two stabilisation elements to obtain the support device according to the disclosure can be carried out without tools, in particular with bare hands. In a preferred embodiment, the at least one snap-in connection, by which the two stabilisation elements of the device according to the disclosure are connected to each other, can subsequently no longer be released without considerable effort.

In a particularly preferred embodiment of the present disclosure, the two stabilisation elements of the support device are configured symmetrically to one another, in particular mirror symmetrically. Preferably, the two stabilisation elements of the support device are configured to be substantially symmetrical to one another, in particular substantially mirror symmetrical, and are connected to one another in the area of the axis of symmetry via at least one snap-in connection.

Particularly preferably, the two stabilisation elements of the support device according to the disclosure are two shell elements. Preferably, the first stabilisation element is a shell element. Preferably, the second stabilisation element is a shell element. Preferably, the first and second stabilisation elements are each shell elements. Particularly preferably, the support device according to the disclosure is a brace-shaped or shell-shaped support device, in particular a brace-shaped or shell-shaped support device comprising two shell elements or consisting of two shell elements.

In a further preferred embodiment of the present disclosure, the two stabilisation elements of the support device are positively connected to one another via at least two, preferably at least three, preferably at least four, snap-in connections.

Particularly preferably, the two stabilisation elements of the support device are positively connected to one another via at least two snap-in connections, wherein a first snap-in connection is configured by engagement of at least one snap-in hook of the first stabilisation element in the at least one retaining element of the second stabilisation element and a second snap-in connection is configured by engagement of at least one snap-in hook of the second stabilisation element in the at least one retaining element of the first stabilisation element.

According to a further preferred embodiment, the two stabilisation elements of the support device are positively connected to one another via at least three snap-in connections, wherein a first snap-in connection is configured by engagement of at least one snap-in hook of the first stabilisation element in the at least one retaining element of the second stabilisation element, a second snap-in connection is configured by engagement of at least one snap-in hook of the second stabilisation element in the at least one retaining element of the first stabilisation element and a third snap-in connection is configured by engagement of at least one snap-in hook of the first stabilisation element in the at least one retaining element of the second stabilisation element. Accordingly, the positively connecting between the two stabilisation elements of the support device is preferably made via at least three snap-in connections, wherein the at least three snap-in connections are configured in an alternating manner, i.e. the first snap-in connection is configured in that at least one snap-in hook arranged on the first stabilisation element engages with at least one retaining element arranged on the second stabilisation element, the second snap-in connection is configured in that at least one snap-in hook arranged on the second stabilisation element engages in at least one retaining element arranged on the first stabilisation element and the third snap-in connection is configured in that at least one snap-in hook arranged on the first stabilisation element engages in at least one retaining element arranged on the second stabilisation element. Due to this arrangement of the snap-in connections between the two stabilisation elements of the support device, it is advantageously not possible to release all snap-in connections simultaneously with a single directed opening impulse. This makes unintentional opening of the support device significantly more difficult, which in turn provides additional safety for the user of the support device.

Preferably, the at least one snap-in hook and the at least one retaining element of the at least one snap-in connection suitable for positively receiving the at least one snap-in hook are integral components of the two stabilisation elements. Preferably, the support device according to the disclosure comprises no further elements in addition to the first and the second stabilisation element. According to this preferred embodiment of the present disclosure, the support device according to the disclosure thus consists of the first and second stabilisation elements, which are positively connected to one another via at least one snap-in connection.

In a further preferred embodiment of the present disclosure, one of the two stabilisation elements comprises a first part of a multi-part connecting element and the other of the two stabilisation elements comprises a second part of the multi-part connecting element, wherein the at least one snap-in hook and the at least one retaining element of the snap-in connection are components of the multi-part connecting element. Preferably, the support device according to the disclosure thus comprises, in addition to the first and second stabilisation elements, a multi-part connecting element, wherein the first and second stabilisation elements are connected to one another via at least one snap-in connection between a first part and a second part of the multi-part connecting element. According to this preferred embodiment of the present disclosure, the support device according to the disclosure consists of two stabilisation elements and a multi-part connecting element. Particularly preferably, the support device according to the disclosure comprises no further elements in addition to the first stabilisation element, the second stabilisation element and the multi-part connecting element.

According to a preferred embodiment of the present disclosure, the multi-part connecting element is a two-part connecting element.

In a further preferred embodiment of the present disclosure, the first part of the multi-part connecting element is releasably connectable, in particular connected, to one of the two stabilisation elements, preferably to the first stabilisation element, preferably to the second stabilisation element. Preferably, the second part of the multi-part connecting element is releasably connectable, in particular connected, to the other of the two stabilisation elements, preferably to the first stabilisation element, preferably to the second stabilisation element. Particularly preferably, the first part of the multi-part connecting element is releasably connectable, in particular connected, to one of the two stabilisation elements and the second part of the multi-part connecting element is releasably connectable, in particular connected, to the other of the two stabilisation elements.

In a preferred embodiment of the present disclosure, the first part of the multi-part connecting element is non-releasably connectable, in particular connected, to one of the two stabilisation elements, preferably to the first stabilisation element, preferably to the second stabilisation element. Preferably, the second part of the multi-part connecting element is non-releasably connectable, in particular connected, to the other of the two stabilisation elements, preferably to the first stabilisation element, preferably to the second stabilisation element. Particularly preferably, the first part of the multi-part connecting element is non-releasably connectable, in particular connected, to one of the two stabilisation elements and the second part of the multi-part connecting element is non-releasably connectable, in particular connected, to the other of the two stabilisation elements.

According to the disclosure, it may be provided that the at least one snap-in connection is configured by reception of at least one snap-in hook of the first stabilisation element or of a first part of a multi-part connecting element in the at least one retaining element of the second stabilisation element or of a second part of a multi-part connecting element.

According to the disclosure, it may also be provided that the at least one snap-in connection is configured by reception of at least one snap-in hook of the first stabilisation element or of a first part of a multi-part connecting element in at least one retaining element of the second stabilisation element or of a second part of a multi-part connecting element and by reception of at least one snap-in hook of the second stabilisation element or of a second part of a multi-part connecting element in at least one retaining element of the first stabilisation element or of a first part of a multi-part connecting element.

According to a particularly preferred embodiment, it may be provided that the two stabilisation elements of the support device are positively connected to one another via at least three snap-in connections between a first and a second part of a multi-part connecting element, wherein a first snap-in connection is configured by engagement of at least one snap-in hook of the first part of the multi-part connecting element in at least one retaining element of the second part of the multi-part connecting element, a second snap-in connection is configured by engagement of at least one snap-in hook of the second part of the multi-part connecting element in at least one retaining element of the first part of the multi-part connecting element, and a third snap-in connection is configured by engagement of at least one snap-in hook of the first part of the multi-part connecting element in at least one retaining element of the second part of the multi-part connecting element. This alternating arrangement of the snap-in connections between the two parts of the multi-part connecting element connecting the stabilisation elements of the support device advantageously prevents unintentional simultaneous opening of all snap-in connections of the support device by a single directed opening impulse.

According to a particularly preferred embodiment of the present disclosure, the at least one snap-in hook comprises a snap-in head and a snap-in nose.

Preferably, the at least one retaining element is an engagement opening with a snap-in edge. Preferably, the snap-in edge is made of an elastic material.

In a preferred embodiment of the present disclosure, the first and second stabilisation elements or the first and second parts of the multi-part closure element each have at least one tongue.

Preferably, the first and second stabilisation elements or the first and second parts of the multi-part closure element each have at least one tongue with at least one snap-in hook arranged on the tongue.

According to a further preferred embodiment of the present disclosure, the first and second stabilisation elements or the first and second parts of the multi-part closure element each have at least one tongue with at least one retaining element arranged on the tongue.

According to a preferred embodiment of the present disclosure, the at least one snap-in hook is arranged on a tongue of the first stabilisation element or of the first part of the multi-part connecting element. Preferably, the at least one snap-in hook is arranged on a tongue of the second stabilisation element or of the second part of the multi-part connecting element.

According to a further preferred embodiment, the at least one retaining element is arranged on a tongue of the first stabilisation element or of the first part of the multi-part connecting element. Preferably, the at least one retaining element is arranged on a tongue of the second stabilisation element or of the second part of the multi-part connecting element.

Particularly preferably, in the connected state of the two stabilisation elements, the tongue penetrates one of the two stabilisation elements, preferably the first stabilisation element, preferably the second stabilisation element, or one of the parts of the multi-part connecting element, preferably the first part of the multi-part connecting element, preferably the second part of the multi-part connecting element, in the area of a through opening, wherein the snap-in hook arranged on the tongue engages on the rear side, i.e. the side facing away from the penetration side, in the retaining element of the respective other stabilisation element, preferably the second stabilisation element, preferably the first stabilisation element, or of the respective other part of the multi-part connecting element, preferably the second part of the multi-part connecting element, preferably the first part of the multi-part connecting element.

According to a further embodiment of the present disclosure, in the connected state of the two stabilisation elements, the tongue penetrates one of the two stabilisation elements, preferably the first stabilisation element, preferably the second stabilisation element, or one of the parts of the multi-part connecting element, preferably the first part of the multi-part connecting element, preferably the second part of the multi-part connecting element, in the area of a through opening, wherein the retaining element arranged on the tongue receives the snap-in hook of one of the two stabilisation elements, preferably the first stabilisation element, preferably the second stabilisation element, or one of the parts of the multi-part connecting element, preferably the first part of the multi-part connecting element, preferably the second part of the multi-part connecting element, arranged on the rear side, i.e. on the side facing away from the penetration side.

In a particularly preferred embodiment of the present disclosure, the penetration of the tongue of one of the two stabilisation elements, preferably the first stabilisation element, preferably the second stabilisation element, or of one of the parts of the multi-part connecting element, preferably the first part of the multi-part connecting element, preferably the second part of the multi-part connecting element, occurs in the area of a through opening of the respective other stabilisation elements, preferably the second stabilisation element, preferably the first stabilisation element, or the respective other part of the multi-part connecting element, preferably the second part of the multi-part connecting element, preferably the first part of the multi-part connecting element, and the rear engagement of the snap-in hook arranged on the tongue in the retaining element or the rear reception of the snap-in hook in the retaining element arranged on the tongue to form a double positive fit, whereby unintentional opening of the stabilisation element is prevented.

In a particularly preferred embodiment of the present disclosure, the at least one snap-in hook comprises a snap-in head and a snap-in nose and the at least one retaining element is an engagement opening with a snap-in edge, wherein the at least one snap-in hook is arranged on a tongue of the first stabilisation element or the first part of the multi-part connecting element, and wherein the tongue in the connected state of the two stabilisation elements penetrates the second stabilisation element or the second part of the multi-part connecting element in the area of a through opening and the snap-in head engages on the rear side in the engagement opening of the second stabilisation element or the second part of the multi-part connecting element.

According to a preferred embodiment of the present disclosure, it may be provided that the supporting device is adjustable in size.

Particularly preferably, the size adjustability of the circumference of the support device is realised by the presence of at least two snap-in hooks arranged next to each other and/or at least two retaining elements of the at least one snap-in connection arranged next to each other.

Preferably, the first stabilisation element or the first part of the multi-part connecting element comprises at least two snap-in hooks arranged next to each other and/or at least two retaining elements arranged next to each other.

In a further preferred embodiment, the second stabilisation element or the second part of the multi-part connecting element comprises at least two snap-in hooks arranged next to each other and/or at least two retaining elements arranged next to each other.

In a particularly preferred embodiment, the first and second stabilisation elements or the first and second parts of the multi-part connecting element, the first stabilisation element or the first part of the multi-part connecting element each comprise at least two snap-in hooks arranged next to each other and/or at least two retaining elements arranged next to each other.

In a further preferred embodiment of the present disclosure, the size adjustability of the circumference of the support device is realised by the interchangeability of the multi-part connecting element. According to this preferred embodiment, the multi-part connecting element is releasably connectable, in particular connected, to the two stabilisation elements of the support device. Preferably, the first part of the multi-part connecting element is releasably connectable, in particular connected, to one of the two stabilisation elements. Preferably, the second part of the multi-part connecting element is releasably connectable, in particular connected, to the other of the two stabilisation elements. According to this preferred embodiment of the present disclosure, the multi-part connecting element, in particular the first and/or second part of the multi-part connecting element, is interchangeable. This makes it possible, for example, to adjust the size of the circumference of the support device by interchanging the multi-part connecting element, in particular the first and/or second part of the multi-part connecting element, with a multi-part connecting element, in particular a first and/or second part of the multi-part connecting element, with the desired dimensioning.

Particularly preferably, the size adjustability of the height of the support device is realised by the presence of detachable segments of the support device.

In a particularly preferred embodiment, the two stabilisation elements are producible, in particular produced, by injection moulding. Preferably, the multi-part connecting element is producible, in particular produced, by injection moulding. In a further particularly preferred embodiment of the present disclosure, the two stabilisation elements and the multi-part connecting element are producible, in particular produced, by injection moulding technology.

According to a further particular embodiment of the present disclosure, it is provided that the supporting device contains at least one perforation, preferably at least two perforations, preferably at least three perforations. In a particularly preferred embodiment, the at least one perforation is located in the area between the two stabilisation elements of the support device. Preferably, the at least one perforation is located in the area between the first and second part of a multi-part connecting element connecting the two stabilisation elements of the support device. In a preferred embodiment, the at least one perforation has a round shape. In a further preferred embodiment of the present disclosure, the at least one perforation has an elliptical shape.

The present disclosure also relates to a method for producing a support device for an orthosis, containing the steps of:

(a) injection moulding two stabilisation elements, and b) positively connecting the two stabilisation elements via at least one snap-in connection to obtain a support device for an orthosis.

Preferably, at least one of the two stabilisation elements has at least one snap-in hook and the other of the two stabilisation elements has at least one retaining element suitable for positively receiving the at least one snap-in hook, wherein the positively connecting in step b) is effected via at least one snap-in connection by receiving the at least one snap-in hook and the at least one retaining element.

In a preferred embodiment of the present disclosure, at least one of the two stabilisation elements has at least one snap-in hook arranged on a tongue. Preferably, at least one of the two stabilisation elements has at least one retaining element suitable for positively receiving a snap-in hook.

Particularly preferably, the positively connecting of the two stabilisation elements takes place in step b) by a tongue of at least one stabilisation element penetrating the other stabilisation element in the area of a through opening and a snap-in hook arranged on the tongue engaging at the rear side in a retaining element of the other stabilisation element.

In a preferred embodiment of the present disclosure, at least one of the two stabilisation elements has a snap-in hook arranged on a tongue and the other of the two stabilisation elements has at least one retaining element suitable for positively receiving the snap-in hook, wherein the positively connecting in step b) takes place via at least one snap-in connection and wherein the tongue of the at least one stabilisation element penetrates the other stabilisation element in the area of a through opening and the snap-in hook arranged on the tongue engages at the rear side in the retaining element of the other stabilisation element.

In a further preferred embodiment, in step a) a multi-part, preferably two-part, connecting element is additionally produced by injection moulding, wherein a first part of the connecting element is connectable to one of the two stabilisation elements and has at least one snap-in hook and a second part of the connecting element is connectable to the other of the two stabilisation elements and comprises at least one retaining element, wherein in step b) a connecting of the first and second parts of the multi-part connecting element with the first and second stabilisation elements takes place and the positively connecting is effected via at least one snap-in connection between the first part of the connecting element and the second part of the connecting element by receiving the at least one snap-in hook in the at least one retaining element.

Particularly preferably, the method according to the disclosure for producing a support device for an orthosis is a method for producing a support device for an orthosis according to the disclosure.

The present disclosure further relates to an orthosis containing a support device according to the present disclosure.

Particularly preferably, the orthosis is selected from the group consisting of knee joint orthosis, hip orthosis, thigh orthosis, back orthosis, in particular spinal orthosis, neck brace, neck stiffener, wrist orthosis, ankle orthosis, elbow orthosis and shoulder joint orthosis. Preferably, the orthosis is a back orthosis, in particular a spinal orthosis.

It is also an object of the present disclosure to use at least one snap-in connection for positively connecting two stabilisation elements of a support device for an orthosis.

Further embodiments of the present disclosure are apparent from the dependent claims.

In the context of the present disclosure, the terms "comprising" and "having" are understood to mean that, in addition to the elements explicitly included by these terms, further elements not explicitly mentioned may be added. In the context of the present disclosure, these terms are also understood to mean that only the explicitly mentioned elements are included and that no further elements are present. In this particular embodiment, the meaning of the terms "comprising" and "having" is synonymous with the term "consisting of". Furthermore, the terms "comprising" and "having" also encompass compositions which, in addition to the explicitly mentioned elements, also contain further elements which are not mentioned but which are of a functionally and qualitatively subordinate nature. In this embodiment, the terms "comprising" and "having" are synonymous with the term "consisting essentially of".

In the context of the present disclosure, the term "and/or" is understood to mean that all members of a group which are connected by the term "and/or" are disclosed both alternatively to each other and cumulatively to each other in any combination. This means for the expression "A, B and/or C" that the following disclosure content is to be understood: a) A or B or C or b) (A and B) or c) (A and C) or d) (B and C) or e) (A and B and C).

The present disclosure is illustrated below with reference to exemplary figures. The inventive concept is not limited to these embodiments.

FIG. 1*a* schematically shows the inside of a support device (100) according to the disclosure for a lumbar back orthosis for the human body. The support device (100) of the embodiment shown comprises two stabilisation elements (110, 120) and a multi-part connecting element (140), via which the first stabilisation element (110) is positively connected to the second stabilisation element (120) via snap-in connections (130*a*, 130*b*, 130*c*).

Figure 1B:
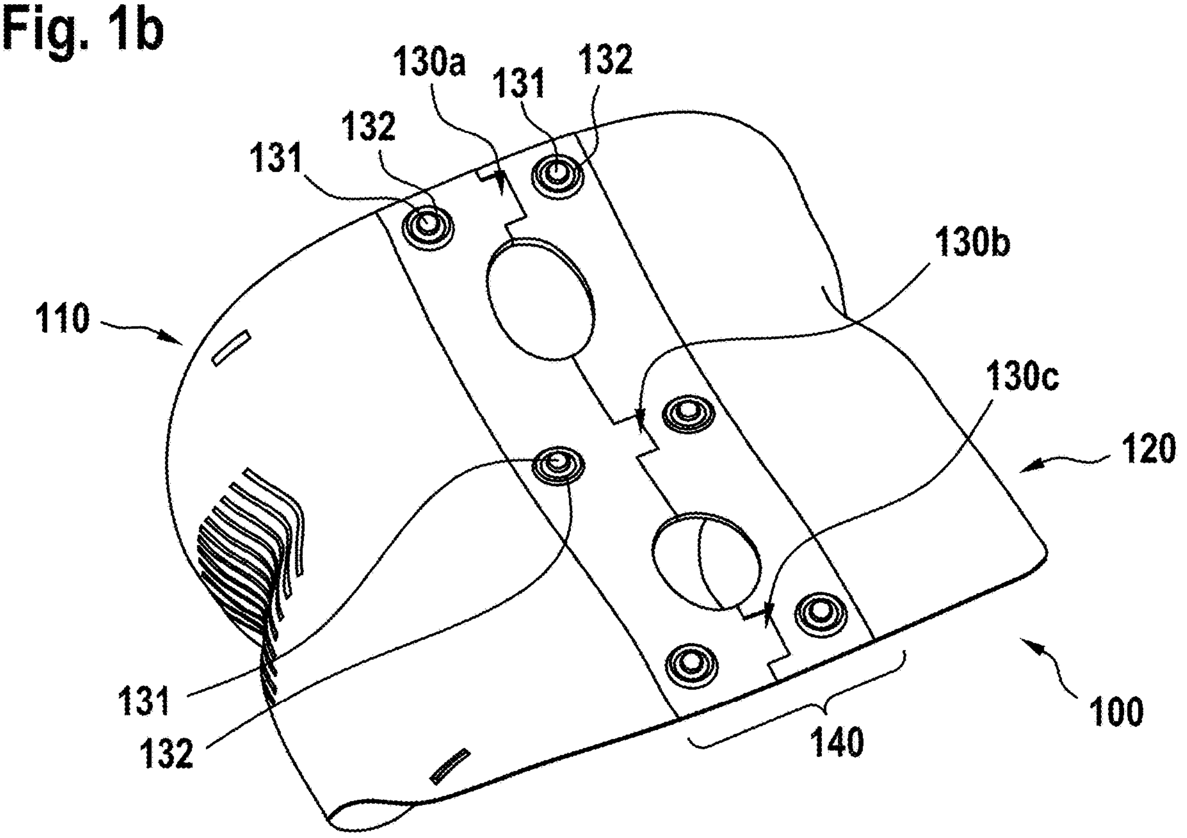
FIG. 1*b* schematically shows the outside of a support device according to one embodiment.

FIG. 1*b* schematically shows the outside of a support device (100) according to the disclosure. In the embodiment of the disclosure shown, the snap-in connections (130*a*, 130*b*, 130*c*) are each configured by the engagement of a snap-in hook (131) of a first part of the multi-part connecting element (140) in a retaining element (132) of a second part of the multi-part connecting element (140) and the engagement of a snap-in hook (131) of the second part of the multi-part connecting element (140) in a retaining element (132) of the first part of the multi-part connecting element (140).

Figure 2A:
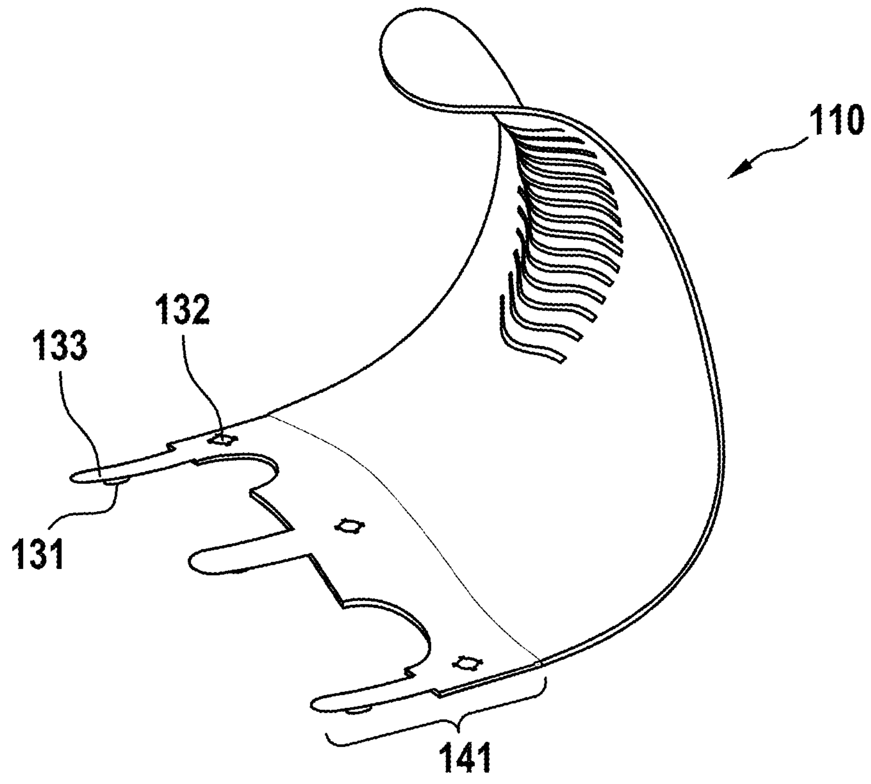
FIG. 2*a* shows the first stabilisation element with a first part of the multi-part connecting element in the disconnected state of a support device according to one embodiment.

FIG. 2*a* shows the first stabilisation element (110) with a first part of the multi-part connecting element (141) in the disconnected state of a support device (100) according to the disclosure. In the embodiment shown, the first part of the multi-part connecting element (141) comprises three tongues (133) suitable for the formation of snap-in connections with snap-in hooks (131) arranged thereon and three retaining elements (132) suitable for receiving snap-in hooks (131).

Figure 2B:
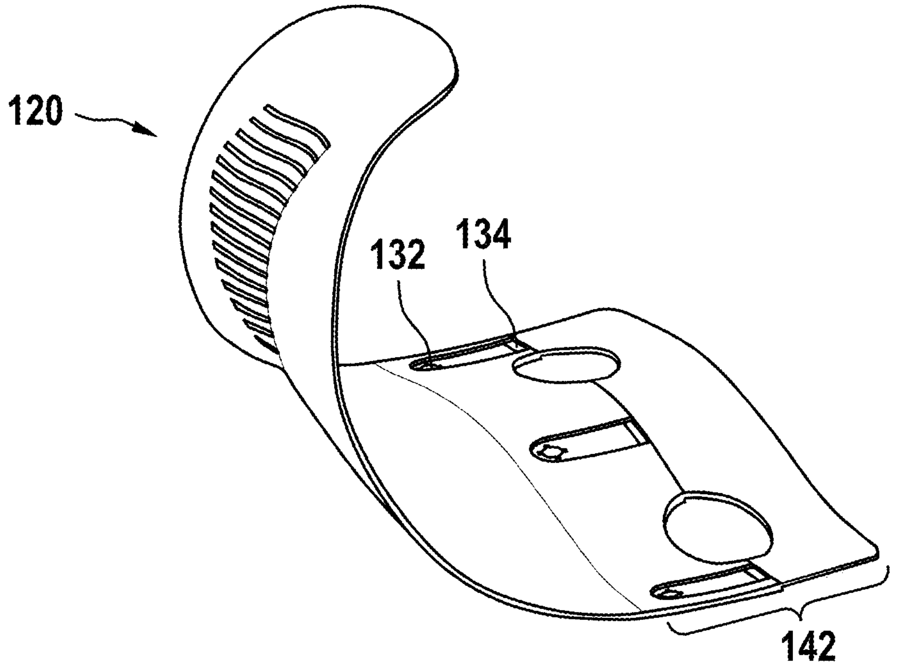
FIG. 2*b* shows the second stabilisation element with a second part of the multi-part connecting element in the disconnected state of a support device according to the one embodiment.

FIG. 2*b* shows the second stabilisation element (120) with a second part of the multi-part connecting element (142) in the disconnected state of a support device (100) according to the disclosure. In the embodiment shown, the second part of the multi-part connecting element (142) comprises three retaining elements (132) suitable for receiving snap-in hooks (131), three through openings (134) for guiding a tongue (133) therethrough of the first part of the multi-part connecting element (141) and snap-in hooks (131) arranged on the side of the second part of the multi-part connecting element (142) not shown.

Figure 3A:
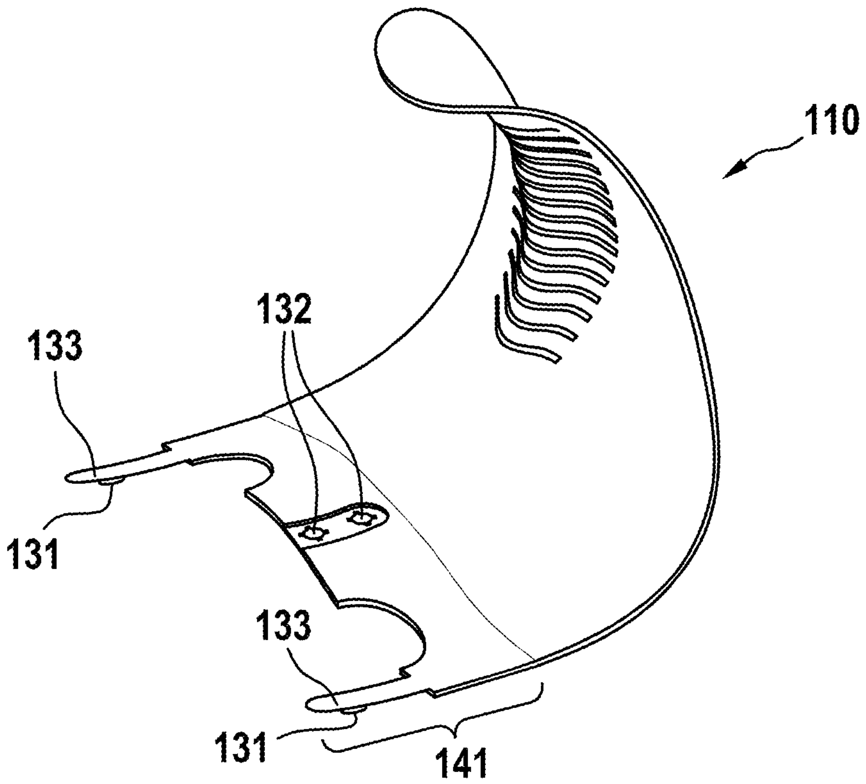
FIGS. 3*a* and 3*b* show a particular embodiment of a support device according to the disclosure, in which the first stabilisation element has a first part of the multi-part connecting element and the second stabilisation element has a second part of the multi-part connecting element.
Figure 3B:
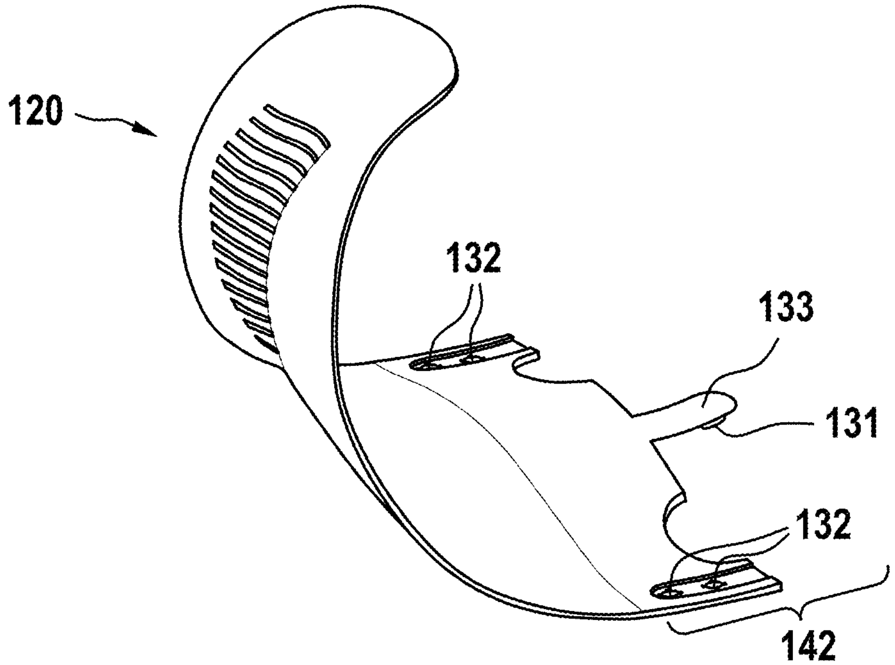

FIGS. 3*a* and 3*b* show a particular embodiment of a support device according to the disclosure, in which the first stabilisation element (110) has a first part of the multi-part connecting element (141) and the second stabilisation element (120) has a second part of the multi-part connecting element (142). According to the embodiment shown, the two stabilisation elements (110, 120) of the support device are positively connectable to one another via three snap-in connections, wherein a first snap-in connection is configured by engagement of a snap-in hook (131), arranged on a tongue (133), of the first part of the multi-part connecting element (141) in a retaining element (132) of the second part of the multi-part connecting element (142), a second snap-in connection is configured by engagement of a snap-in hook (131) of the second part of the multi-part connecting element (142), which is arranged on a tongue (133), in a retaining element (132) of the first part of the multi-part connecting element (141), and a third snap-in connection is configured by engagement of a snap-in hook (131) of the first part of the multi-part connecting element (141), which is arranged on a tongue (133), in a retaining element (132) of the second part of the multi-part connecting element (142). In the embodiment shown, the first (141) or second part (142) of the multi-part connecting element (140) have two spaced-apart retaining elements (132) arranged next to each other for adjusting the size of the circumference.

Figure 4A:
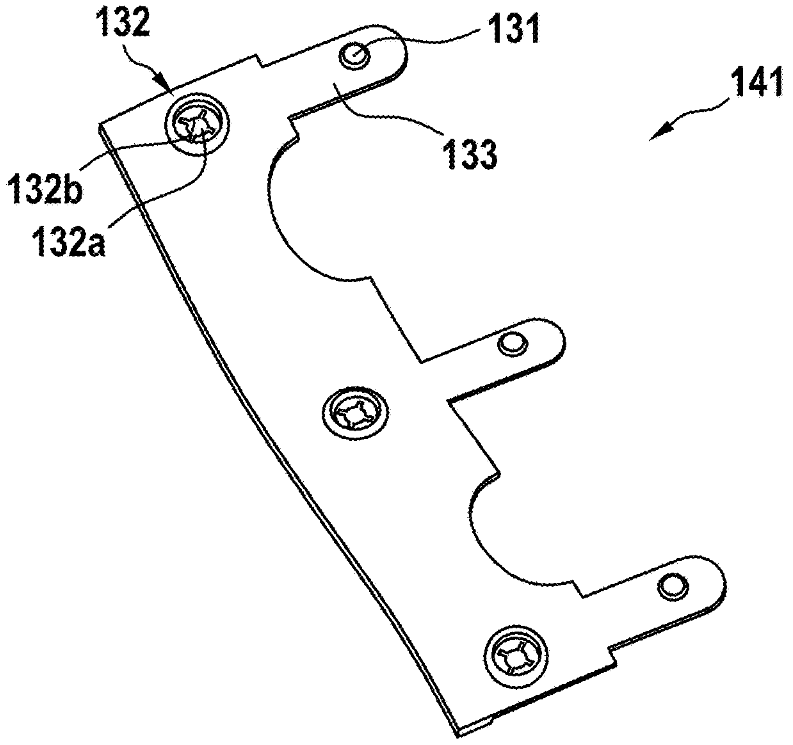
FIG. 4*a* shows a first part of a multi-part connecting element comprising a snap-in hook arranged on a tongue.

FIG. 4*a* shows a first part of a multi-part connecting element (141) comprising a snap-in hook (131) arranged on a tongue (133), which serves for engagement in a retaining element (132) of a second part of a multi-part connecting element (142), and a retaining element (132) with an engagement opening (132*a*) with a snap-in edge (132*b*), which serves for receiving a snap-in hook (131) of the second part of a multi-part connecting element (142).

Figure 4B:
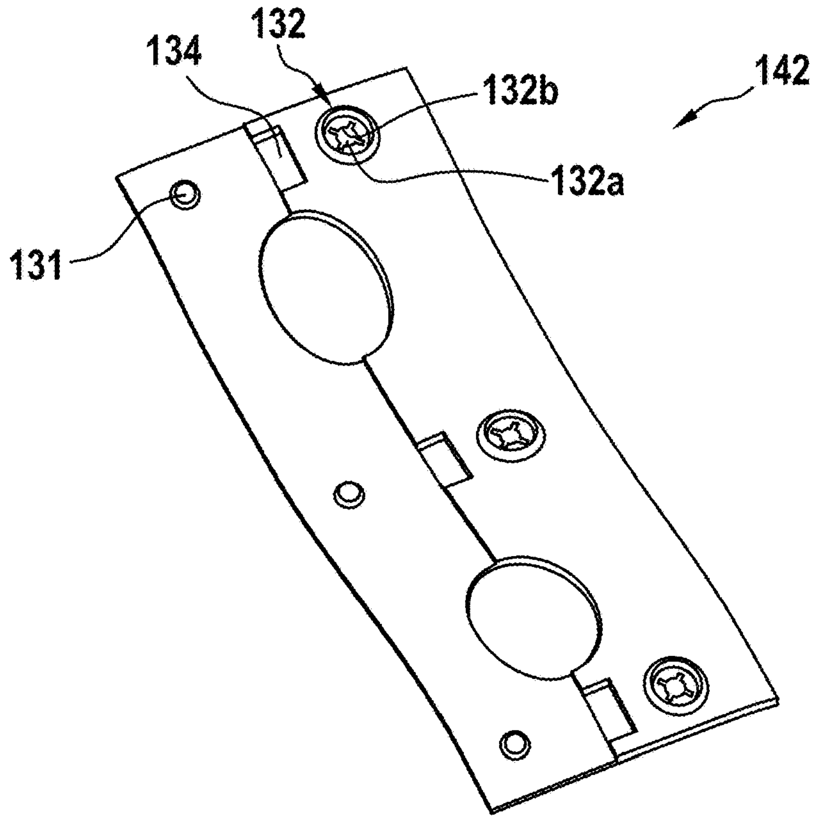
FIG. 4*b* schematically shows the second part of one of the multi-part connecting elements.

FIG. 4*b* schematically shows the second part of one of the multi-part connecting elements (142). This comprises a snap-in hook (131), which serves for engagement in a retaining element (132) of the first part of a multi-part connecting element (141), a retaining element (132) with an engagement opening (132*a*) with a snap-in edge (132*b*), which serves for receiving a snap-in hook (131) of the first part of a multi-part connecting element (141), and a through opening (134) through which a tongue (133) of the first part of the multi-part connecting element (141) is guided, so that the snap-in hook (131) arranged on the tongue (133) of the first part of the multi-part connecting element (141) can engage at the rear side in the engagement opening (132*a*) of the second part of the multi-part connecting element (142).

Figure 5A:
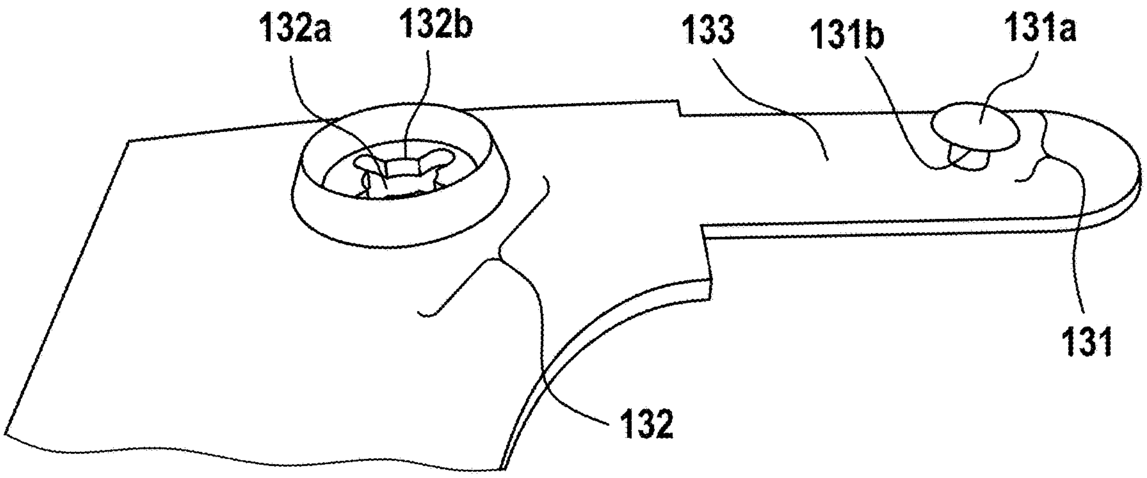
FIG. 5*a* schematically shows a section of the first part of a multi-part connecting element.

FIG. 5*a* schematically shows a section of the first part of a multi-part connecting element (141). A snap-in hook (131) arranged on a tongue (133) is shown, which serves for engagement in a retaining element (132) of a second part of a multi-part connecting element (142) and has a snap-in head (131*a*) and a snap-in nose (131*b*). Furthermore, FIG. 5*a* shows a retaining element (132) with an engagement opening (132*a*) and a snap-in edge (132*b*), which serves to receive a snap-in hook (131) of the second part of a multi-part connecting element (142).

Figure 5B:
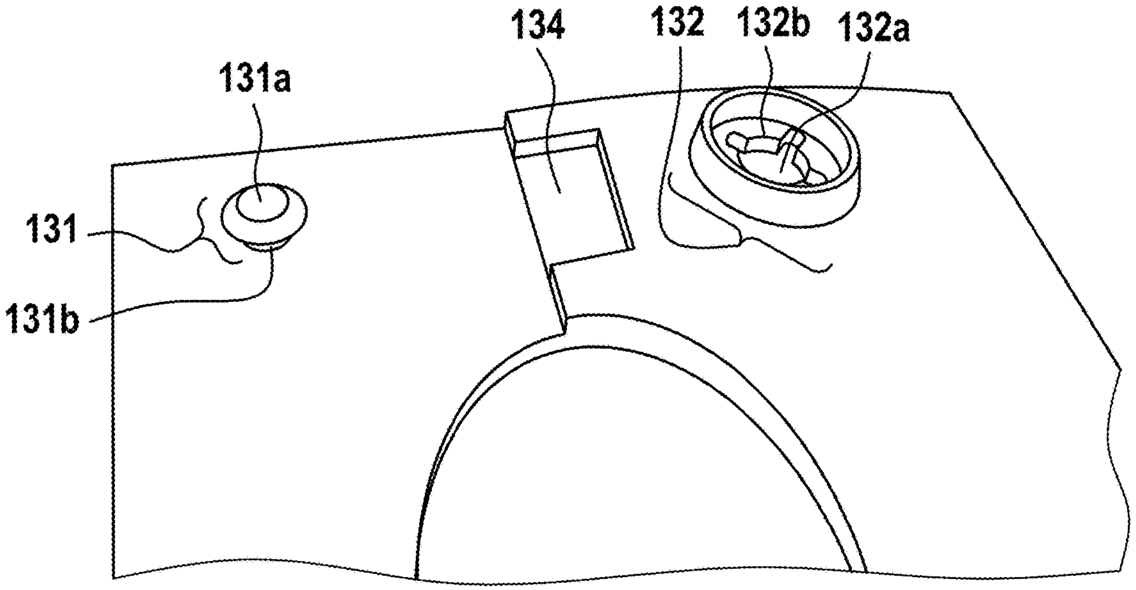
FIG. 5*b* schematically shows a section of the second part of a multi-part connecting element.

FIG. 5*b* schematically shows a section of the second part of a multi-part connecting element (142). The section shows a snap-in hook (131), which comprises a snap-in head (131*a*) and a snap-in nose (131*b*), a through opening (134) through which a tongue (133) of the first part of the multi-part connecting element (141) is guided, and a retaining element (132), which comprises an engagement opening (132*a*) and a snap-in edge (132*b*).

The invention claimed is:

1. A multi-part support device for an orthosis which is brace-shaped or shell-shaped and configured to predominantly encompass a body part in its total circumference and comprises two single shell elements which each extend over less than half of a total circumference of the body to be encompassed, wherein the two single shell elements of the multi-part support device are positively connected to one another via at least two snap-in connections, wherein each of the two single shell elements, or a first part and a second part of a multi-part connecting element arranged between the two single shell elements, has at least one snap-in hook and at least one retaining element, wherein the at least one snap-in hook and the at least one retaining element of the snap-in connections suitable for positively receiving the at least one snap-in hook are integral components of the two shell elements or the first part and the second part of the multi-part connecting element, and wherein a first snap-in connection is configured by engagement of at least one snap-in hook of a first shell element or the first part of the mu1ti-part connecting element in the at least one retaining element of a second shell element or the second part of the multi-part connecting element; and a second snap-in connection is configured by engagement of at least one snap-in hook of the second shell element or the second part of the multi-part connecting element in the at least one retaining element of the first shell element or the first part of the multi-part connecting element.

2. The multi-part support device of claim 1, wherein in that the two shell elements of the support device are positively connected to one another via at least three snap-in connections, wherein a first snap-in connection is configured by engagement of at least one snap-in hook of the first shell element or the first part of the multi-part connecting element in the at least one retaining element of the second shell element or the second part of the multi-part connecting element, a second snap-in connection is configured by engagement of at least one snap-in hook of the second shell element or the second part of the multi-part connecting element in the at least one retaining element of the first shell element or the first part of the multi-part connecting element, and a third snap-in connection is configured by engagement of at least one snap-in hook of the first shell element or the first part of the multi-part connecting element in the at least one retaining element of the second shell element or the second part of the multi-part connecting element.

3. The multi-part support device of claim 1, wherein the first part of the multi-part connecting element is releasably connectable to one of the two shell elements and the second part of the multi-part connecting element is releasably connectable to the other of the two shell elements.

4. The multi-part support device of claim 1, wherein the at least one snap-in hook comprises a snap-in head and a snap-in nose and the at least one retaining element is an engagement opening with a snap-in edge, wherein the at least one snap-in hook is arranged on a tongue of the first shell element or the first part of the multi-part connecting element, wherein the tongue in a connected state of the two shell elements penetrates the second shell or the second part of the multi-part connecting element in an area of a through opening and the snap-in head engages on a rear side in the engagement opening of the second shell element or the second part of the multi-part connecting element.

5. The multi-part support device of claim 1, wherein the two shell elements are producible by injection moulding.

6. A method for producing a multi-part support device for an orthosis, comprising:

a) injection moulding two shell elements comprising a first shell element and a second shell element, wherein each of the two shell elements has at least one snap-in hook and at least one retaining element suitable for positively receiving the snap-in hook, and wherein the at least one snap-in hook and the at least one retaining element are integral components of the two shell elements; and b) positively connecting the two shell elements via at least two snap-in connections to obtain a brace-shaped or shell shaped multi-part support device for an orthosis, wherein a first snap-in connection is configured by engagement of at least one snap-in hook of the first shell element in the at least one retaining element of the second shell element and a second snap-in connection is configured by engagement of at least one snap-in hook of the second shell element in the at least one retaining element of the first shell element.

7. The method of claim 6, wherein at least one of the two shell elements has a snap-in hook arranged on a tongue wand the other of the two shell elements has at least one retaining element suitable for positively receiving the snap-in hook, wherein the positively connecting in step b) takes place via at least one snap-in connection and wherein the tongue of one of the two shell elements penetrates the other of the two shell elements in an area of a through opening and the snap-in hook arranged on the tongue engages at a rear side in the retaining element of the other shell element.

8. An orthosis containing a multi-part support device of claim 1.

9. The orthosis of claim 8, selected from the group consisting of knee joint orthosis, hip orthosis, thigh orthosis, back orthosis, in particular spinal orthosis, neck brace, neck stiffener, wrist orthosis, ankle orthosis, elbow orthosis and shoulder joint orthosis.

10. A curved multi-part support device for an orthosis configured to predominantly encompass a body part in its total circumference comprises:

two shell elements, including a first shell element and a second shell element, each of the two shell elements extending over less than half of a total circumference of the body part to be encompassed, wherein the two shell elements of the support device are positively connected to one another via at least two snap-in connections, wherein each of the two shell elements, or a first part and a second part of a multi-part connecting element arranged between the two shell elements, has at least one snap-in hook and at least one retaining element, wherein the at least one snap-in hook and the at least one retaining element of the snap-in connections suitable for positively receiving the at least one snap-in hook are integral components of the two shell elements or the first part and the second part of the multi-part connecting element, and wherein a first snap-in connection is configured by engagement of at least one snap-in hook of the first shell element or the first part of the multi-part connecting element in the at least one retaining element of the second shell element or the second part of the multi-part connecting element; and a second snap-in connection is configured by engagement of at least one snap-in hook of the second shell element or the second part of the multi-part connecting element in the at least one retaining element of the first shell element or the first part of the multi-part connecting element.

* * * * *